United States Patent [19]

Sasaki

[11] 4,422,326
[45] Dec. 27, 1983

[54] METHOD OF ASCERTAINING THE STATE INSIDE MELTING FURNACE FOR RADIOACTIVE WASTE

[75] Inventor: Noriaki Sasaki, Tokai, Japan

[73] Assignee: Doryokuro Kakunenryo Kaihatsu Jigyodan, Tokyo, Japan

[21] Appl. No.: 266,063

[22] Filed: May 19, 1981

[30] Foreign Application Priority Data

Aug. 26, 1980 [JP] Japan .................... 55-117342

[51] Int. Cl.³ .................................. G01F 23/14
[52] U.S. Cl. ............................ 173/291; 73/302; 73/439
[58] Field of Search ............. 73/291, 302, 439, 64.4

[56] References Cited
U.S. PATENT DOCUMENTS 3,881,344  5/1975  Jobe .................................. 73/64.4

OTHER PUBLICATIONS

"Instrument Society of America Journal" Aug. 1954, pp. 23-24.

Primary Examiner—James J. Gill
Attorney, Agent, or Firm—Wenderoth, Lind & Ponack

[57] ABSTRACT

A method of ascertaining the state inside a melting furnace of a radioactive waste, which method comprises: blowing a gas into a molten matter in the melting furnace by using at least two slender tubes disposed at an upper and lower points with a gap $\Delta h$ between said points; detecting a back pressure difference $\Delta P$ at the slender tubes to determine the density $\rho$ of the molten matter; and determining the level h of the molten matter in the furnace using the density $\rho$. It is also possible to detect the formation of a bridge inside the furnace due to a non-molten solid matter of the waste charged into the furnace.

4 Claims, 5 Drawing Figures

METHOD OF ASCERTAINING THE STATE INSIDE MELTING FURNACE FOR RADIOACTIVE WASTE

BACKGROUND OF THE INVENTION

This invention relates to a method capable of accurately ascertaining the state inside a melting furnace employed for immobilizing a radioactive waste in glass, glass ceramics, synthetic rocks and stones, and so forth.

It has been attempted to immobilize and solidify radioactive waste in glass or the like in order to safely and economically store or treat nuclear fission products and radioactive nuclides such as transuranium elements that are contained in the radioactive waste. Research and development in this respect has therefore been made in various countries of the world. When the radioactive waste is immobilized and solidified in the glass, it is first charged into a melting furnace in the liquid state (including a slurry) or in the solid state, is then melted together with the glass and is thereafter withdrawn into a separate container. This method is customary in the art. In order to accomplish a safe and stable operation of the melting furnace in this instance, it is necessary to accurately measure quantities of contents (such as molten glass, unmolten liquid, slurry and its dried and calcined matter, other solid matter, etc.) inside the furnace, their positions inside the furnace and changes in their quantities and positions. Requirements imposed on measuring instruments for this purpose are that they are easy to carry out remote operation, trouble-free and small in size and have high reliabilty because one cannot directly operate or maintain these instruments due to high radioactive intensity around the melting furnace.

In the glass industry, there have conventionally been employed various devices for measuring the level of glass such as, for example, ultrasonic level meters, radiation level meters, electrostatic capacitance type level meters, level meters using thermo-couples, electrode type level meters, and the like. However, these level meters cannot easily be applied to the glass melting furnace used with radioactive waste because their operability, reliability, service life, maintenance, and the like are adversely affected.

Especially when the raw material in the liquid or slurry form is charged into the furnace and is melted with glass, some may be dried and calcined on the surface of the molten matter to thereby form hard solid matter that is, when the raw material is charged into the furnace faster than it can be melted by the molten glass. The solid matter thus formed covers in turn the surface of the molten matter and produces a hard bridge. In such a state, gases, which are primarily generated when the solid matters is melted, accumulate in a space between the molten glass and the bridge of the solid matter, thus elevating the pressure in the space and resulting in furnace damage. Moreover, if the bridge is broken, the gases blow strongly into the furnace and upset the pressure balance. In the case of an over-flow type melting furnace, the glass in the melting furnace is pushed down while the glass at a fore hearth portion is pushed up, thereby also upsetting the pressure balance. If the molten glass alone is withdrawn from the furnace under such conditions where the solid matter forms a bridge, only the level of the glass lowers while the bridge of the solid matter remains as such so that a large cavity is produced under the bridge. In this state, heat conduction from the molten glass diminishes so that the speed at which the solid matters melts decreases and a fall down of the bridge of the solid matter is likely to occur. Accordingly, it is of the utmost importance for the safe operation of the melting furnace to ascertain whether or not the solid matter forms the bridge inside the melting furnace. A conventional method available heretofore for this purpose is to look into and examine the furnace from an inspection window of the furnace. For this reason, development of a suitable detection method has been desired.

SUMMARY OF THE INVENTION

An object of the present invention is, therefore, to provide a method which is capable of accurately ascertaining the state inside a melting furnace for a radioactive waste and which is simple in construction but has a high reliability.

Another object of the present invention is to provide a method for simply detecting the level and the density of a molten matter and changes in the level and the density thereof inside a melting furnace for a radioactive waste.

A further object of the present invention is to provide a method for accurately detecting the presence or absence of a bridge formed during the melting of a radioactive waste charged into a melting furnace for the radioactive waste.

To accomplish the abovementioned objects, the present invention fundamentally utilizes a conventional bubble-type level measuring method and makes it possible to accurately ascertain varying conditions inside the melting furnace.

Such a bubble-type level measuring method is based on the fundamental principle that a minimum pressure P required for releasing bubbles from a slender tube inserted perpendicularly into a liquid is given by the following equation:

$$P = 2\gamma/r + \rho g h + P_o \qquad (1)$$

where:
 $\gamma$: surface tension of liquid
 r: radius of slender tube
 $\rho$: density of liquid
 g: gravitational acceleration
 h: depth of liquid
 $P_o$: pressure on liquid surface.

The radius r of the slender tube can be selected optionally while the surface tension $\gamma$ of the liquid as well as its density $\rho$ are the basic properties of the liquid and can be measured beforehand. Accordingly, the depth of the liquid or the level h, can be determined in accordance with the following equation by measuring the pressure difference $P - P_o$:

$$h = \frac{P - P_o - 2\gamma/r}{\rho g} \qquad (1')$$

Though many examples are known in which the abovementioned bubble-type level measuring method is adapted to a level meter, no example has been known in which the measuring method is adapted to the level measurement in the melting furnace for the radioactive waste. This is because, in the melting furnace, the density of the liquid changes in accordance with a matter to be molten so that accurate level measurement cannot be made relying simply upon the abovementioned equation (1'). Another reason may be attributed to the fact that the bubble-type level measurement cannot easily be applied to molten glass that has a considerably large density and viscosity.

The present invention is accomplished on the basis of the concept that the bubble-type level measurement can be applied even to the melting furnace for the radioactive waste, and accurate level measurement can be made by performing density correction, and it is also possible to detect the presence or absence of the bridge formed by the waste charged into the furnace.

According to the present invention, there is provided a method of ascertaining the state inside a melting furnace for a radioactive waste, which method comprises: blowing a gas into a molten matter in the melting furnace by using a least two slender tubes disposed at an upper and lower points with a gap $\Delta h$ between said points; detecting a back pressure difference $\Delta P$ at the slender tubes to determine the density $\rho$ of the molten matter in accordance with a equation $\rho = \Delta P / g \cdot \Delta h$ (where g is gravitational acceleration); and determining the level h of the molten matter in the furnace using the density $\rho$ above-mentioned and in accordance with the equation (1').

According to the present invention, it is also possible to detect the formation of a bridge inside the furnace due to non-molten solid matter of the waste charged into the furnace by obtaining beforehand the relationship between a quantity of the charged waste and the pressure P in a normal case where the charged waste is molten in the furnace, and detecting a shift of the pressure P from said relationship obtained beforehand.

PREFERRED EMBODIMENTS OF THE INVENTION

Figure 1:
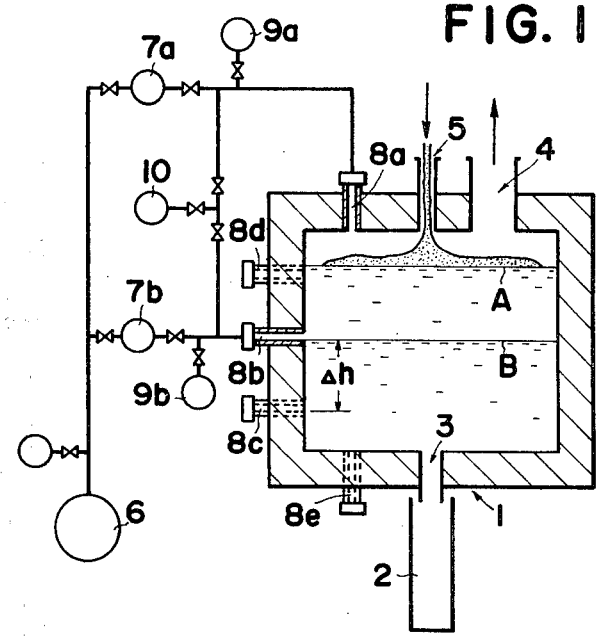
FIG. 1 is a schematic view showing an apparatus which can be used to perform the method of the present invention.

Referring now to FIG. 1, a glass melting furnace 1 is equipped, at its bottom, with a glass discharging port 3 for a glass receiver 2 and, at its upper portion, with an off-gas outlet 4 and with a charging port 5 of radioactive waste to be treated. Gas from a compressed gas source 6 is subjected to pressure control to a predetermined pressure by a pressure regulating valve at its outlet and is so controlled by a flow meters 7a, 7b as to attain a predetermined flow rate. Thereafter, the gas is allowed to flow into the furnace through slender tubes 8a, 8b that are disposed through the furnace wall. The pressure P of the slender tube 8b is measured by a pressure gauge 9b, and the pressure $P_o$ inside the furnace 1 is separately measured by the slender tube 8a and a pressure gauge 9a. The pressure difference $P - P_o$ is determined by a differential pressure gauge 10 and, from the thus determined pressure difference, a value constantly corresponding to the glass level h can be calculated in accordance with the aforementioned equation (1').

In this embodiment of FIG. 1, there are employed one gas-purging slender tube 8a at the upper portion of the melting furnace 1, with three gas-purging slender tubes 8b, 8c, 8d at its side and one gas-purging slender tube 8e at its bottom. However, the positions and number of these slender tubes are not restrictive, in particular, and they may be optionally arranged. As tubes such as 8b, 8c, by way of example, must be disposed below the molten glass level in order to carry out density measurement of the molten matter. Namely, using the two upper and lower gas-purging slender tubes 8b, 8c disposed below the molten glass level in the spaced-apart arrangement by a gap $\Delta h$, the gas is blown and the difference in back pressure $\Delta P$ in this instance is determined. From this difference in the back pressure $\Delta P$, the accurate density $\rho$ of the molten glass can be measured in accordance with the following equation (2):

$$\rho = \Delta P / g \cdot \Delta h \qquad (2)$$

Since the positions and radii of the gas-purging slender tubes are given in advance, the depth and quantity of the molten matter and their changes can be accurately determined from the pressure indication, the size and shape of the furnace and the density of the molten matter. Incidentally, it has been found that in the case of molten glass in general, a constant value may be employed for the surface tension $\gamma$ of the liquid, because its temperature coefficient is small within the ordinary operating temperature range even when the operating temperature changes to some extent or even when a certain temperature distribution exists inside the furnace.

In FIG. 1, when the glass is discharged from the state of the glass level A, indication of the pressure difference $P - P_o$ becomes smaller in proportion to the decrease in the level and becomes substantially zero when the glass level passes by the slender tube position B. Accordingly, the level of the molten glass can be detected at this point. If the set position of the slender tubes 8a for the level meter is suitably determined, detection of the upper limit or lower limit of the glass quantity inside the furnace 1 can be made effectively.

There is no limitation to the position of the tip of the gas-purging tubes 8e, in particular. However, if the tubes are to be disposed at the bottom or on the side wall of the furnace, it is preferred for the purpose of minimizing corrosion of the slender tubes by the glass that the tip of each tube be placed on the same plane as, or considerably inwardly relative to, the inner surface of the furnace wall. For the same reason, this arrangement is superior to the construction in which the slender tube is suspended from the upper part of the furnace.

The diameter of the slender tubes 8a–8e and the gas-purging flow rate may sufficiently be about 1 to 4 mm and about 40 Nl/hour, respectively. However, if the gas pressure is so controlled as to be equal to P of the equation (1), the level can be measured without causing the gas to flow. So long as the gas is purged, it does not happen that the slender tube can; not be used any longer as the glass or the like enters the tube and solidifies in it. In order to enable re-use of the slender tube if the glass or the like enters and clogs the tube by any chance, it is preferred to employ such a construction in which a heater or the like is disposed around the slender tube for the purpose of heating, or such a construction in which the slender tube itself generates the heat (by direct feed of current, for example) by selecting the tube material or other necessary means.

Figure 2:
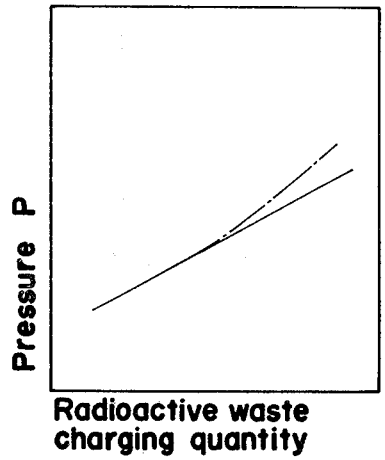
FIG. 2 is a diagram showing the pressure shift at the time of formation of the bridge.

In accordance with the present invention, it is also possible to detect the presence or absence of the bridge due to charge of the radioactive waste into the melting furnace. Namely, if the non-molten solid matter of the radioactive waste is not melted by the molten glass as fast as it is charged into the furnace and the solid matter therefore covers the surface of molten matter and forms the hard bridge, there is caused the accumulation of gas produced at the time of melting of the solid matter to thereby increase the pressure in a space between the bridge and the molten glass. Thus, as shown by a dot-dash line in FIG. 2, the pressure P of the gas-purging slender tube shifts towards a value which is higher than the normal pressure change (represented by solid line in FIG. 2) caused by the increase in the molten glass level resulting from the increase of the charging quantity of the radioactive waste. Accordingly, formation of the bridge can be detected from the occurrence of this shift, and if charge of the radioactive waste is stopped at this point, possible accidents that might result from the bridge formation can be avoided.

Figure 3:
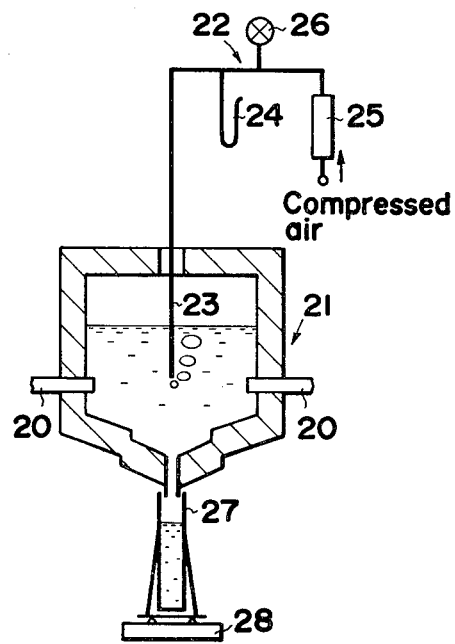
FIG. 3 is a schematic view of the experimental apparatus for practicing the present invention.
Figure 4:
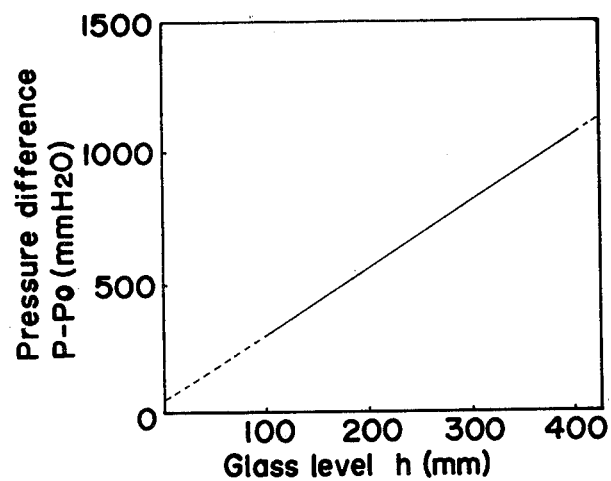
FIG. 4 is a diagram showing an example of the relationship between the glass depth and the pressure difference.

An experimental example to illustrate the effectiveness of the method of the present invention will now be described. FIG. 3 is a schematic view showing an apparatus used for the experiment. Glass containing a simulated radioactive waste is melted inside a direct current feed type glass melting furnace 21 (sectional area inside the furnace=0.3 m²) equipped with a molybdenum electrode 20, and a bubble type level meter 22 is installed in the furnace from its upper portion to carry out the experiment. The level meter 22 comprises a gas-purging slender tube 23, a manometer 24, a purging set 25, a differential pressure gauge cell 26, and the like. A molten glass receiver 27 disposed below the furnace is placed on a load cell 28 so that the discharging quantity of the molten glass can also be measured by the load cell 28. FIG. 4 illustrates the relationship between the glass depth h and the pressure difference $P-P_o$ when the measurement is carried out using air as the purging gas, a glass temperature of 1,200° C., a radius of 1.2 mm for the purging slender tube and the air flow rate of 10 Nl/hour. It is obvious from this graph that the pressure difference $P-P_o$ is proportional to the glass depth h and the line can be expressed by the following equation (3):

$$P-P_o = 2.57h + 50 \quad (3)$$

The unit of the pressure difference $P-P_o$ is mmH$_2$O and that of the glass depth h, mm. The glass density at 1,200° C. is found to be 2.57 (g/cm³) and the surface tension is found to be about 290 dyn/cm. When the experiments are carried out at temperatures of 1,000° and 1,100° C., respectively, substantially the same results can be obtained.

Figure 5:
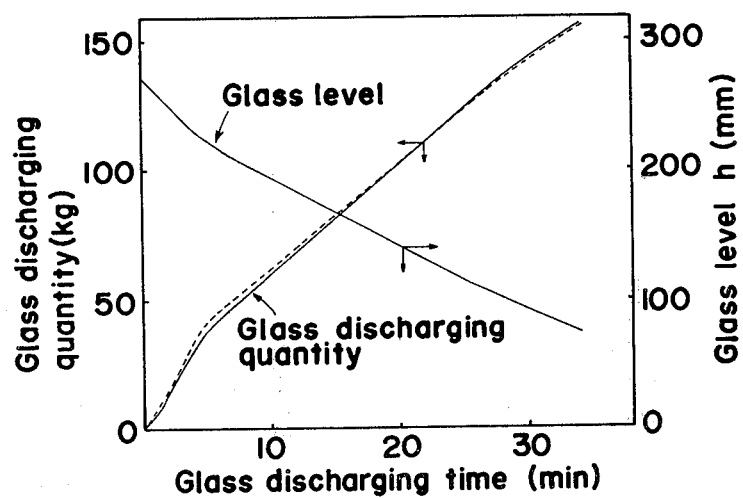
FIG. 5 is a diagram showing an example of the changes in the glass level and in the discharging quantity.

FIG. 5 is a graph showing the relationship between the change in the glass level and the glass discharging quantity as the result of the actual measurement when the molten glass is discharged from the furnace. The glass depth h is this graph is the value calculated by using the relationship expressed by the equation (3). The glass discharging quantity represented by solid line is measured by actually measuring the change in the weight of the glass discharging receiver 27 placed at the lower part of the furnace by the load cell 28. The glass discharging quantity represented by the dotted line is calculated from the change in the glass depth, the glass density and the cross-sectional area inside the furnace. The actually measured value of the glass discharging quantity obtained in this experiment, in which 155 kg glass is discharged, is in good agreement with the value calculated from the measured pressure value of the bubble type glass level meter. Thus, it is obvious that the method of the present invention is effective.

As described in the foregoing, the present invention provides a method of ascertaining the state inside the furnace using the principle of the conventional bubble type level meter. Accordingly, the present invention only requires such a simple construction in which the quantity to be measured is only the back pressure of the gas-purging slender tube and the slender tube may as well be installed on the furnace wall of the melting furnace exposed to the high radioactive intensity. As can be understood from the abovementioned experimental example, the method of the invention can provide high reliability, and makes it possible to accurately ascertain not only the level, density and changes in the level and density of the molten matter, but also the absence or presence of the bridge which might be formed during the melting of the charged radioactive waste. Hence, the method of the present invention is extremely useful for the safe and stable operation of the melting furnace for the radioactive waste over an extended period of time.

What is claimed is:

1. A method of ascertaining the state inside a melting furnace for a radioactive waste, which method comprises the steps of:
   (1) blowing a gas into a molten matter in the melting furnace by using a least two slender tubes including a first tube opening into the furnace at an upper point thereof and a second opening into the furnace at a lower point thereof with a gap Δh between the upper and lower points;
   (2) detecting a back pressure difference ΔP at the openings of the first and second tubes to determine the density ρ of the molten matter in accordance with the following equation:

$$\rho = \Delta P / g \cdot \Delta h$$

where g is the gravitational acceleration;
   (3) detecting a minimum pressure P required for releasing gas bubbles into the molten matter from one of the at least two slender tubes;
   (4) determining the level h of the molten matter in the furnace using the density determined in step (2) and in accordance with the following equation:

$$h = \frac{P - P_O - 2\gamma/r}{\rho g},$$

where
   $P_O$ is the pressure on the surface of the molten matter,
   γ is the surface tension of the molten matter, and
   r is the radius of the one of the at least two slender tubes;
   (5) determining the relationship between a quantity of the waste charged into the melting furnace and the pressure P in a normal case where the charges waste is molten in the furnace; and (6) monitoring the pressure P to detect a shift of the pressure P from the relationship obtained in step (5) to thereby detect the formation of a bridge inside the furnace comprising non-molten solid matter of the charged waste.

2. A method as in claim 1, wherein the molten matter comprises molten glass.

3. A method as in claim 1, wherein said step (6) includes the step of detecting a rapid decrease in the pressure P to thereby detect a breakage of the bridge.

4. A method of ascertaining the state inside a melting furnace for a radioactive waste, which method comprises the steps of:
  (a) blowing a gas into a molten matter in the melting furnace by use of a slender tube opening into the furnace;
  (b) detecting a minimum pressure P required for releasing gas bubbles into the molten matter from the slender tube;
  (c) determining the relationship between a quantity of the waste charged into the melting furnace and the pressure P in a normal case where the charged waste is molten in the furnace; and
  (d) monitoring the pressure P to detect the shift of the pressure P from that determined in step (c) to thereby detect the formation of a bridge inside the furnace comprising a non-molten solid matter of the charged waste when the shift is an increase in the pressure P, and to thereby detect a breakage of the bridge when the pressure P experiences a rapid decrease.

* * * * *